(12) United States Patent
Tanter et al.

(10) Patent No.: US 11,766,242 B2
(45) Date of Patent: Sep. 26, 2023

(54) METHOD AND DEVICE FOR MAPPING FIBROUS MEDIA

(71) Applicant: Centre National de La Recherche Scientifique—CNRS, Paris (FR)

(72) Inventors: Mickaël Tanter, Bagneux (FR); Mathias Fink, Meudon (FR); Mathieu Pernot, Paris (FR); Clément Papadacci, Paris (FR)

(73) Assignee: CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 1502 days.

(21) Appl. No.: 14/904,013

(22) PCT Filed: Jul. 16, 2014

(86) PCT No.: PCT/FR2014/051829
§ 371 (c)(1),
(2) Date: Jan. 8, 2016

(87) PCT Pub. No.: WO2015/007992
PCT Pub. Date: Jan. 22, 2015

(65) Prior Publication Data
US 2016/0151046 A1   Jun. 2, 2016

(30) Foreign Application Priority Data
Jul. 19, 2013   (FR) .................... 13 57158

(51) Int. Cl.
*A61B 8/00*   (2006.01)
*G01S 15/89*   (2006.01)
*G01S 7/52*   (2006.01)

(52) U.S. Cl.
CPC ............ *A61B 8/4494* (2013.01); *A61B 8/463* (2013.01); *G01S 7/52036* (2013.01);
(Continued)

(58) Field of Classification Search
CPC ......... A61B 8/4494; A61B 8/463; A61B 8/52; A61B 8/5207; G01S 7/52085;
(Continued)

(56) References Cited

U.S. PATENT DOCUMENTS

2013/0109971 A1   5/2013   Dahl et al.
2014/0046173 A1*  2/2014   Greenleaf .......... G01N 29/2456
                                                    600/430

FOREIGN PATENT DOCUMENTS

EP   2 101 191 A2   9/2009

OTHER PUBLICATIONS

W. Lee et al., "Mapping Myocardial Fiber Orientation Using Echocardiography-Based Shear Wave Imaging," in IEEE Transactions on Medical Imaging, vol. 31, No. 3, pp. 554-562, Mar. 2012 http://ieeexplore.ieee.org/stamp/stamp.jsp?tp=&arnumber=6054058 &isnumber=6159236 (Year: 2012).*

(Continued)

*Primary Examiner* — Chao Sheng
(74) *Attorney, Agent, or Firm* — Osha Bergman Watanabe & Burton LLP

(57) ABSTRACT

A method for mapping fibrous media by propagation of ultrasound from a set transducers, wherein: a number of unfocused incident ultrasonic waves having different wavefronts are emitted; the signals reverberated by the medium toward each transducer are captured; coherent signals respectively corresponding, for each transducer, to contributions coming from different fictitious focal points in the medium are determined; and then the orientation of the fibers is determined by comparing a spatial coherence between said coherent signals, in a plurality of directions.

11 Claims, 1 Drawing Sheet

(52) U.S. Cl.
CPC ...... *G01S 7/52085* (2013.01); *G01S 15/8925* (2013.01); *G01S 15/8977* (2013.01); *G01S 15/8997* (2013.01)

(58) Field of Classification Search
CPC ............. G01S 7/52036; G01S 15/8925; G01S 15/8977; G01S 15/8997
See application file for complete search history.

(56) References Cited

OTHER PUBLICATIONS

Papadacci et al.; Towards backscatter tensor imaging (BTI): Analysis of the spatial coherence of ultrasonic speckle in anisotropic soft tissues; published on Jul. 25, 2013; 2013 IEEE International Ultrasonics Symposium (IUS); Date of Conference: Jul. 21-25, 2013; p. 1208-1211 (Year: 2013).*

Papadacci et al.; Shear Wave Imaging of the heart using a cardiac phased array with coherent spatial compound; published on Oct. 10, 2012; 2012 IEEE International Ultrasonics Symposium; Date of Conference: Oct. 7-10, 2012; p. 2023-2026 (Year: 2012).*

International Search Report for related International Application No. PCT/FR2014/051829; report dated Jul. 10, 2014.

Wei-Ning Lee et al: "Noninvasive assessment of myocardial anisotropy in vitro and in vivo using Supersonic Shear Wave Imaging", Ultrasonics Symposium (IUS), 2010 IEEE, IEEE, Oct. 11, 2010 (Oct. 11, 2010), pp. 690-693, XP031953033, DOI: 10.1109/ULTSYM. 2010.5935898 ISBN: 978-1-4577-0382-9 abrégé p. 691, colonne de droite—alinéa C.-D.

Motaldo G et al: Coherent plane-wave compounding for very high frame rate ultrasonography and transient elastography, IEEE Transactions on Ultrasonics, Ferroelectrics and Frequency Control, IEEE, US, vol. 56, No. 3, Mar. 1, 2009 (Mar. 1, 2009), ISSN: 0885-3010 cité dans la demande abrégé.

Bastien Denarie et al: "Coherent Plane Wave compounding for very High Frame Rate Ultrasonography of Rapidly Moving Targets", IEEE Transactions on Medical Imaging, IEEE Service Center, Piscataway, NJ, US, vol. 32, No. 7, Jul. 1, 2013 (Jul. 1, 2013), pp. 1265-1276, XP011516355, ISSN: 0278-0062, DOI: 10.1109/TMI. 2013.2255310 cité dans la demande abrégé.

Wei-Ning Lee et al: "Mapping myocardial Fiber Orientation Using Echocardiography-based SheaR Wave Imaging", IEEE Transactions on Medical Imaging, vol. 31, No. 3, Mar. 2012.

Wei-Ning Lee et al: "Ultrasound Elastic Tensor Imaging: Comparison with MR Diffusion Tensor Imaging in the Myocardium" Institute Langevin, ESPCI ParisTech, Paris, France, Received Jan. 31, 2012, in final form Jun. 28, 2012, Published Jul. 27, 2012, Online at stacks.iop.org/PMB/57/5075, DOI:10.1088/0031-9155/57/16/5075.

Arnaud Derode and Mathias Fink "Spatial Coherence of Ultrasonic Speckle in Composites" IEEE Transactions on Ultrasonics, Ferroelectrics, and Frequency Control, vol. 40, No. 6, Nov. 1993.

* cited by examiner

METHOD AND DEVICE FOR MAPPING FIBROUS MEDIA

CROSS-REFERENCE TO RELATED APPLICATION

This Application is a 35 USC § 371 US National Stage filing of International Application No. PCT/FR2014/051829 filed on Jul. 16, 2014, and claims priority under the Paris Convention to French Patent Application No. 13 57158 filed on Jul. 19, 2013.

FIELD OF THE DISCLOSURE

The present invention relates to methods and devices for mapping fibrous media.

BACKGROUND OF THE DISCLOSURE

Such a method has already been described, for example by Derode and Fink (*Spatial coherence of ultrasonic speckle in composites*, Derode A., M. Fink, *IEEE Trans Ultrason Ferroelectr Freq Control* 1993; 40(6):666-75), which teaches the successive emission of ultrasonic waves focused by a transducer array placed on the surface of a composite material, with multiple orientations of the transducer array. For each ultrasonic wave firing, a function of the spatial coherence between signals captured by the transducers after reverberation of the transmitted ultrasonic wave is calculated, and the direction of the fibers of the composite material is determined as being the direction of the transducer array corresponding to the maximum of the spatial coherence function.

This known method is suitable for a simple medium such as a composite material in which the fibers are regularly arranged; it is not appropriate for studying a more complex medium such as biological tissue.

However, there is a need to map the structure of biological tissues composed of fibers, such as myocardial, muscle, and brain tissue. This structure plays a crucial role in both the mechanical function (muscle tissue) and the electrical function (brain, muscle, heart) of these tissues, and the spatial orientation of the fibers is therefore a very important parameter to determine for diagnostic purposes and for functional exploration of these bodies.

For example, in brain imaging, it is very important to identify the neuronal fiber pathways that connect different brain areas. Currently, the only technology able to provide a three-dimensional image of the organization of fibers is magnetic resonance imaging by diffusion tensor (diffusion MRI). This very slow technique is used for exploration of the adult brain, but is too limited for imaging moving organs such as the heart. Also, MRI is not used to image the brains of very young children, especially premature babies who may have brain development abnormalities which unfortunately are impossible to diagnose with current techniques.

SUMMARY OF THE DISCLOSURE

The present invention is intended to overcome these disadvantages.

To this end, the invention provides a method for mapping fibrous media, comprising:

(a) a measurement step during which a set of transducers $T_{ij}$ emits, in a field of view of a medium comprising fibers, a number N of unfocused incident ultrasonic waves (meaning not focused in the field of view) l having different wavefronts, and respective signals $RFraw_{l,ij}(t)$ representative of ultrasonic waves reverberated by the medium are captured by the transducers $T_{ij}$ from the incident waves l, (b) a step of synthesizing coherent data during which are determined, from N sets of captured signals $RFraw_{l,ij}(t)$, for a number M of fictitious focal points $P_k$ in the field of view, coherent signals $RFcoherent_{k,ij}(t)$ corresponding to the signals that would have been received by the transducers $T_{ij}$ if a wave focused at point $P_k$ had been emitted by said transducers, (c) a step of mapping fibers of the medium, during which the presence and orientation of fibers at each point $P_k$ are determined by comparing a spatial coherence between coherent signals $RFcoherent_{k,ij}(t)$ in a plurality of directions.

It is thus possible to map very quickly and easily the structure of biological tissues composed of fibers, such as the myocardium and other muscles and the brain, due to the fact that the backscattered signals contain information about the tissue microstructure that is not directly visible in the ultrasound image (B mode). It is the analysis of spatial coherence which reveals the orientation of the fibers, because the tissue anisotropy is found in the coherence function measured in different directions.

In various embodiments of the method according to the invention, one or more of the following arrangements may possibly be used:

- during step (a), the set of transducers used is a two-dimensional transducer array;
- during step (c), an integral of a function of spatial coherence between transducers is determined in a plurality of directions, and the direction of the fibers is determined as being a direction which maximizes said integral;
- the incident ultrasonic waves are plane waves having different propagation directions;
- the incident ultrasonic waves are divergent waves (emitted by the ultrasound array as if they came from different source points);
- the incident ultrasonic waves are emitted successively;
- the incident ultrasonic waves are encoded spatiotemporally and emitted simultaneously, then the reverberated waves are captured simultaneously and separated by decoding;
- an image of the fibers detected in the medium is displayed;
- an ultrasound image of the field of view is determined and this ultrasound image is displayed with a superimposed image of the fibers;
- the ultrasound image is determined by beamforming the coherent signals determined in step (b);
- the medium to be imaged is human or animal tissue (particularly mammalian).

The invention also relates to a device for implementing a mapping method as defined above, comprising a set of transducers $T_{ij}$ as well as control and processing means suitable for:

(a) causing the set of transducers $T_{ij}$ to emit, in a field of view of a medium comprising fibers, a number N of incident ultrasonic waves l having different wavefronts, and causing the transducers $T_{ij}$ to capture respective signals $RFraw_{l,ij}(t)$ representative of reverberated ultrasonic waves from the incident waves l, (b) determining, from the N sets of captured signals $RFraw_{l,ij}(t)$, for a number M of fictitious focal points $P_k$ in the field of view, coherent signals $RFcoherent_{k,ij}(t)$ corresponding to the signals that would have been received by the transducers $T_{ij}$ if a wave focused at point $P_k$ had been emitted by said transducers, (c) determining the presence and orientation of fibers at each point $P_k$, by comparing functions of spatial coherence between the signals RFcoherent$_{k,ij}$ (t) in a plurality of directions.

Advantageously, the set of transducers is two-dimensional.

BRIEF DESCRIPTION OF THE DRAWINGS

Other features and advantages of the invention will be apparent from the following description of one of its embodiments, given by way of non-limiting example with reference to the accompanying drawings.

In the drawings.

DETAILED DESCRIPTION OF THE DISCLOSURE

In the various figures, the same references designate identical or similar elements.

Figure 1:
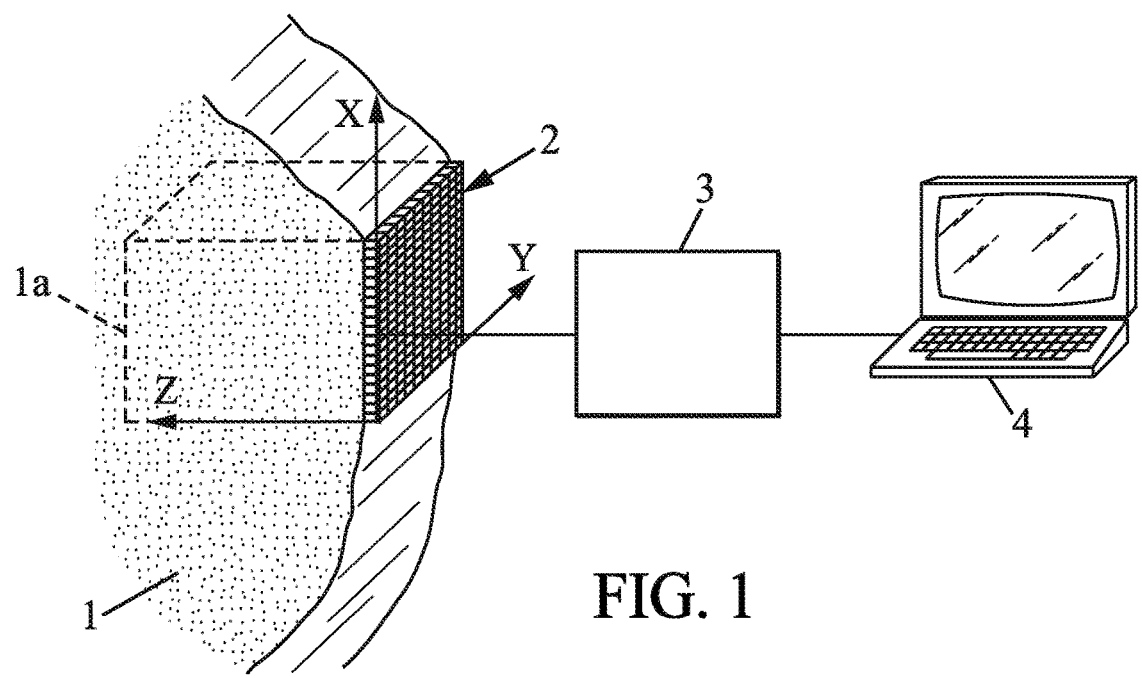
FIG. 1 is a schematic view of a device for implementing a method according to an embodiment of the invention.

FIG. 1 shows an exemplary imaging device that operates by emitting and receiving ultrasonic compression waves, for example in the frequency range of 2 to 40 MHz.

The imaging device represented in FIG. 1 is adapted for performing synthetic ultrasound imaging of a field of view 1a in a fibrous medium 1, for example tissue of a patient, particularly a muscle (myocardium or other muscle) or the brain.

The imaging device comprises, for example:
- an array 2 of n ultrasonic transducers, for example a two-dimensional array comprising for example several hundred transducers and adapted for obtaining a three-dimensional (3D) image of the field of view 1a;
- an electronics bay 3 or the like for controlling the transducer array 2 and adapted for acquiring the signals captured by the transducer array;
- a computer 4 or the like for controlling the electronics bay 3 and viewing the ultrasound images obtained from said captured signals.

The transducer array 2 may, for example, be a planar matrix extending along two perpendicular axes X,Y, with the Z axis perpendicular to the X, Y axes denoting the depth direction in the field of view. In what follows, the transducers will be denoted $T_{ij}$, i and j being the two indices denoting the position of each transducer respectively along the X and Y axes. The transducer array 2 may in particular comprise $n_1$ transducers in the X direction and $n_2$ transducers in the Y direction, with $n=n_1*n_2$. The following description uses this type of transducer array 2 for its example, but other forms of transducer array are also possible within the scope of the invention.

Figure 2:
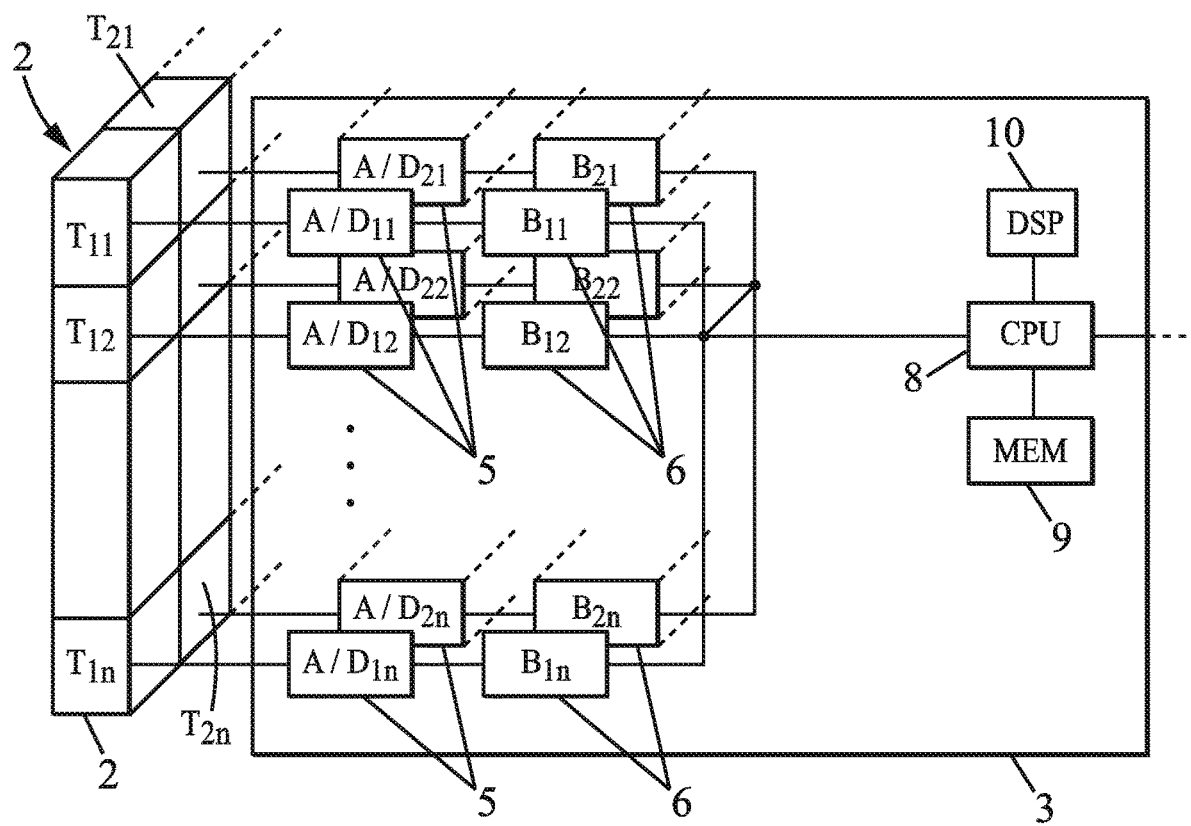
FIG. 2 is a block diagram of a portion of the device of FIG. 1.

As represented in FIG. 2, the electronics bay 3 may comprise for example:
- n analog-to-digital converters 5 (A/D$_{ij}$) connected individually to the n transducers $T_{ij}$ of the transducer array 2,
- n buffers 6 (B$_{ij}$) respectively connected to the n analog-to-digital converters 5,
- a central processing unit 8 (CPU) communicating with the buffers 6 and the computer 4,
- a memory 9 (MEM) connected to the CPU 8,
- a digital signal processor 10 (DSP) connected to the CPU 8.

This device allows implementing a method for mapping the fibers of the medium 1, which includes in particular the following three steps carried out by the CPU 8 with the assistance of the digital signal processor 9:
a) measurement (emission/reception and recording of raw data)
b) synthesis of coherent data,
c) analysis of fiber orientation,
d) optionally, determining an image of the medium in B mode and superimposing the fiber mapping.

Step a: Measurement (Emission/Reception and Recording of Raw Data):

The transducer array is placed in contact with the medium 1 and a number N of incident ultrasonic waves is emitted into the medium 1 by the transducers $T_{ij}$ (N may be for example between 2 and 100, in particular between 5 and 10). The incident waves in question are unfocused (more specifically, not focused in the field of view) and have different respective wavefronts, meaning wavefronts of different shapes and/or different orientation. Advantageously, the incident waves are plane waves of various different inclinations, characterized by their respective angles of inclination $\alpha_X$, $\alpha_Y$ relative to the Z axis, respectively in planes (X, Z) and (Y, Z), or are divergent waves emitted as if they originated from different points in space.

The incident waves are generally pulses of less than a microsecond, typically about one cycle of the ultrasonic wave at the center frequency. The firing of incident waves may be spaced apart, for example by about 50 to 200 microseconds.

Each incident wave encounters reflectors in the medium 1, which reverberate the incident wave. The reverberated ultrasonic wave is captured by the transducers $T_{ij}$ of the array. This signal captured by each transducer $T_{ij}$ comes from the medium 1 as a whole, since the incident wave is not focused at emission.

Reverberant signals captured by the n transducers $T_{ij}$ are then digitized by the corresponding analog-to-digital converters A/D$_{ij}$ and stored in the corresponding buffers B$_{ij}$. These signals stored in the buffers after each incident firing will be referred to hereinafter as raw RF data ("RF" is a term conventionally used in the field, simply because of the ultrasound frequency used). These raw RF data consist of an array of $n_1*n_2$ time signals RFraw$_{l,ij}$(t) respectively captured by the transducers $T_{ij}$ after the firing of incident ultrasonic waves l.

After each firing of incident waves l, the signals stored in the buffers B$_{ij}$ are transferred to the memory 9 of the signal processor 8 for processing by said processor. At the end of step (a), the memory 9 therefore contains N arrays of raw RF signals.

Note that the various incident waves could be spatiotemporally encoded, to allow simultaneous emission of some or all of the incident waves and an also simultaneous reception of the reverberated waves, which are then separated by decoding prior to storing them.

Step b: Synthesis of Coherent RF Data

From N arrays of raw RF data, a number M of arrays of synthetic coherent RF data is calculated by the processor 8, respectively at M points $P_k$(x, y, z) of the field of view 1a (k being an integer between 1 and M, and x, y, z being the coordinates of point $P_k$ on the X, Y, Z axes). Each of these M arrays of synthetic coherent RF data contains $n_1*n_2$ time signals RFcoherent$_{k,ij}$(t) corresponding to the signals which would respectively be captured by the transducers $T_{ij}$ if the transducers were emitting a focused incident wave at point $P_k$.

The arrays of coherent RF data may be obtained for example by assuming a uniform propagation speed c throughout the medium 1 for ultrasonic compression waves, according to the principle explained in particular in document EP2101191 or in the article by Montaldo et al. "Coherent plane-wave compounding for very high frame rate ultrasonography and transient elastography" (IEEE Trans Ultrason Ferroelectr Freq Control 2009 March; 56(3): 489-506.

As the direction of propagation of the plane wave corresponding to each firing 1 is known, and the propagation speed c is known, the processor 8 can calculate for each point $P_k$ the propagation time $\tau_{ec}(l,k)$ of the incident wave 1 to point $P_k$, and the propagation time $\tau_{rec}(l, k, i, j)$ of the reverberated wave from point $P_k$ to transducer $T_{ij}$, therefore the total time to travel in both directions $$\tau(l,k,i,j)=\tau_{ec}(l,P_k)+\tau_{rec}(l,P_k,i,j).$$

The spatially coherent signal for transducer $T_{ij}$, corresponding to virtual focal point $P_k$, is then calculated using the formula:

$$RFcoherent_{kij}(t) = \sum_l B(l) RFraw_{lij}(\tau(l, k, i, j)) \quad (1)$$

where B(l) is a weighting function for the contribution of each firing of incident waves l (in the current case, the values of B(l) may be all equal to 1).

The arrays of coherent data $RFcoherent_k$ may then possibly be refined by correcting the effects of aberrations in the medium 1, for example as explained in the aforementioned documents EP2101191 or Montaldo et al.

Step c: Analysis of Fiber Orientation

Next a spatial coherence is determined, for each array RFcoherent, indicative of the coherence between signals $RFcoherent_{kij}(t)$ for a same point $P_k$.

This spatial coherence can be measured for example by a spatial coherence function R(m) calculated using the correlations of signals $c_k(ij,pq)$ received on transducers ij and pq, by summing all correlations between pairs of remote transducers of m elements in a given direction in plane (X, Y).

$$c(ij, tu) = \sum_{T1}^{T2} \left( RFcoherent_{k,ij}(t) - \overline{RFcoherent_{k,ij}} \right) \quad (2)$$

$$\left( RFcoherent_{k,tu}(t) - \overline{RFcoherent_{k,tu}} \right)$$

where $\overline{RFcoherent_{k,ij}}$ is a temporal mean of $RFcoherent_{k,ij}$, and T1, T2 are two times.

By considering only the transducers aligned with each other in a same direction of plane (X, Y) and renumbering these transducers Tq, q from 1 to Q, these correlations can be written as c(p, q) and we obtain:

$$c(p, q) = \sum_{T1}^{T2} \left( RFcoherent_{k,p}(t) - \overline{RFcoherent_{k,p}} \right) \quad (2a)$$

$$\left( RFcoherent_{k,q}(t) - \overline{RFcoherent_{k,q}} \right)$$

$$R(m) = \frac{Q}{Q-m} \frac{\sum_{q=1}^{Q-m} c(q, q+m)}{\sum_{q=1}^{Q} c(q, q)} \quad (3)$$

The Van Cittert-Zernike theorem establishes the shape of this function R(m) in a randomly reflecting medium (therefore isotropic) for a monochromatic beam. R(m) is the spatial Fourier transform of the square of the focal spot. For a focal spot whose lateral extension is given by a function sin(ax)/x, R(m) is a triangle whose apex is at m=0 (autocorrelation) and which cancels out at m=Q.

For a non-isotropic medium, additional spatial coherence is obtained when the direction of alignment of the transducers is aligned along the fibers.

The integral $S_k$ of this function in the considered direction of alignment in plane (X, Y) gives a parameter of spatial coherence, which is maximized in the fiber alignment direction. By calculating this parameter of spatial coherence in a plurality of alignment directions of the transducers, one can discover the direction producing the maximum spatial coherence parameter $S_k$ and thus deduce the direction of the fibers at point $P_k$.

Note that the abovementioned spatial coherence functions R(m) or the spatial coherence parameters $S_k$ could be averaged over several neighboring points $P_k$, therefore within a small volume of the field of view around a point of interest.

Another possible spatial coherence parameter is the focus criterion $C_k$, which gives the ratio between coherent energy and incoherent backscattered energy. With the above notation, in other words by numbering from q=1 to Q the transducers aligned along a same direction in plane (X, Y), we have:

$$C_k = \frac{\left\langle \left| \sum_{q=1}^{Q} RFcoherent_{k,q}(t-t_q) \right|^2 \right\rangle}{Q \sum_{q=1}^{Q} \left\langle |RFcoherent_{k,q}(t-t_q)|^2 \right\rangle} \quad (4)$$

where $t_q$ is a delay which allows rephasing all the signals $RFcoherent_{k,q}(t)$.

As in the previous case, this spatial coherence parameter is calculated in several directions for each point $P_k$, and the direction of the fibers is determined as being the direction that maximizes parameter Ck.

One can thus very quickly determine a three-dimensional mapping of fibers of the medium within the field of view 1a. This mapping can advantageously be presented to the user of the device in the form of cross-sectional images of the medium 1, for example displayed on the screen of the computer 4. If desired, these images can be calculated with restoration of continuity between fibers detected at different points $P_k$.

Step d: Image Formation

From the arrays $RFcoherent_k$ calculated in step (b), it is possible to form a three-dimensional B-mode image of the field of view 1a by beamforming, as described for example in the aforementioned document EP2101191.

It is possible to superimpose the fiber mapping determined in step (c) onto this B-mode image, and cross-sectional images of the field of view can be displayed on the screen of the computer, showing both the B-mode image and the fibers superimposed on this image.

The invention claimed is:

1. A method for mapping fibrous media, comprising:
a measurement step during which a set of transducers emits, in a field of view of a medium comprising fibers, a plurality of successive unfocused incident ultrasonic waves having different wavefronts, wherein the set of transducers is a two-dimensional transducer array, wherein said plurality of successive unfocused incident ultrasonic waves successively propagate in the field of view without focusing in said field of view, and wherein said plurality of successive unfocused incident ultrasonic waves are successively reverberated by the medium and captured by said set of transducers to produce sets of captured signals, wherein solely said successive unfocused incident ultrasonic waves are transmitted to the medium,
a step of synthesizing coherent data to determine coherent signals from said sets of captured signals and for a number M of fictitious focal points Pk in the field of view, wherein the coherent signals correspond to signals that would have been received by the set of transducers if a wave focused at a fictitious focal point Pk had been emitted by said set of transducers, and
a step of mapping fibers of the medium comprising calculating, at each fictitious focal point Pk, a spatial coherence parameter in a plurality of alignment directions of said set of transducers, using a measure of spatial coherence between said coherent signals,
wherein the spatial coherence parameter is based on no shear wave imaging, and
wherein mapping the fibers of the medium is based on determining the presence and orientation of fibers at each fictitious focal point Pk using the spatial coherence parameter.

2. The method according to claim 1 wherein the spatial coherence parameter is an integral of functions of spatial coherence between the coherent signals, and the direction of the fibers at each fictitious focal point Pk is determined as being a direction which maximizes said integral.

3. The method according to claim 1, wherein the plurality of successive unfocused incident ultrasonic waves are plane waves having different propagation directions.

4. The method according to claim 1, wherein the plurality of successive unfocused incident ultrasonic waves are divergent waves.

5. The method according to claim 1, wherein the medium to be imaged is human or animal tissue.

6. The method according to claim 1, wherein an image of the fibers detected in the medium is displayed.

7. The method according to claim 6, wherein an ultrasound image of the field of view is determined and this ultrasound image is displayed with a superimposed image of the fibers.

8. The method according to claim 7, wherein the ultrasound image is determined by beamforming the coherent signals determined in the step of synthesizing coherent data.

9. A device for implementing a mapping method, comprising:
a set of transducers arranged in a two-dimensional transducer array and control and processing means configured for:
causing the set of transducers to emit, in a field of view of a medium comprising fibers, a plurality of successive unfocused incident ultrasonic waves having different wavefronts, wherein said plurality of successive unfocused incident ultrasonic waves propagate in the field of view without focusing in said field of view, and causing the set of transducers to capture said plurality of successive unfocused incident ultrasonic waves reverberated by the medium to produce sets of captured signals, wherein solely said successive unfocused incident ultrasonic waves are transmitted to the medium,
determining coherent signals from said sets of captured signals and for a number M of fictitious focal points Pk in the field of view, wherein the coherent signals correspond to signals that would have been received by the set of transducers if a wave focused at a fictitious focal point Pk had been emitted by said set of transducers,
calculating, at each fictitious focal point Pk, a spatial coherence parameter in a plurality of alignment directions of said set of transducers using a measure of spatial coherence between said coherent signals, and
determining the presence and orientation of fibers at each fictitious focal point Pk using the spatial coherence parameter,
wherein the spatial coherence parameter is based on no shear wave imaging.

10. A method for mapping fibrous media, comprising:
a measurement step during which a set of transducers emits, in a field of view of a medium comprising fibers, a plurality of successive unfocused incident ultrasonic waves having different wavefronts, wherein the set of transducers is a two-dimensional transducer array, wherein said plurality of unfocused incident ultrasonic waves successively propagate in the field of view without focusing in said field of view, and wherein said plurality of unfocused incident ultrasonic waves are successively reverberated by the medium and captured by said set of transducers to produce sets of captured signals, wherein solely said unfocused incident ultrasonic waves are transmitted to the medium without propagating shear waves in the medium, wherein no share waves are propagated in the medium,
a step of synthesizing coherent data to determine coherent signals from said sets of captured signals, and for a number M of fictitious focal points Pk in the field of view, wherein the coherent signals correspond to signals that would have been received by the set of transducers if a wave focused at a fictitious focal point Pk had been emitted by said set of transducers, and
a step of mapping fibers of the medium comprising calculating, at each fictitious focal point Pk, a spatial coherence parameter in a plurality of alignment directions of said set of transducers, using a measure of spatial coherence between said coherent signals, and
wherein mapping the fibers of the medium is based on determining the presence and orientation of fibers at each fictitious focal point Pk using the spatial coherence parameter.

11. A device for implementing a mapping method, comprising:
a set of transducers arranged in a two-dimensional transducer array and control and processing means configured for:
causing the set of transducers to successively emit, in a field of view of a medium comprising fibers, a plurality of unfocused incident ultrasonic waves having different wavefronts, wherein said plurality of unfocused incident ultrasonic waves propagate in the field of view without focusing in said field of view, and causing the set of transducers to capture said plurality of unfocused incident ultrasonic waves successively reverberated by the medium to produce sets of captured signals, wherein solely said unfocused incident ultrasonic waves are transmitted to the medium without propagating shear waves in the medium, wherein no share waves are propagated in the medium, determining coherent signals from said sets of captured signals, and for a number M of fictitious focal points Pk in the field of view, wherein the coherent signals correspond to signals that would have been received by the set of transducers if a wave focused at a fictitious focal point Pk had been emitted by said set of transducers, wherein solely said unfocused incident ultrasonic waves are transmitted to the medium, wherein no share waves are propagated in the medium, calculating, at each fictitious focal point Pk, a spatial coherence parameter in a plurality of alignment directions of said set of transducers using a measure of spatial coherence between said coherent signals, and determining the presence and orientation of fibers at each fictitious focal point Pk using the spatial coherence parameter.

* * * * *